United States Patent [19]

Crisp et al.

[11] 4,222,920

[45] * Sep. 16, 1980

[54] CEMENTS

[75] Inventors: Stephen Crisp, Hounslow; Alan D. Wilson, Liphook, both of England

[73] Assignee: National Research Development Corporation, England

[ * ] Notice: The portion of the term of this patent subsequent to Apr. 5, 1994, has been disclaimed.

[21] Appl. No.: 901,786

[22] Filed: May 1, 1978

Related U.S. Application Data

[63] Continuation of Ser. No. 724,394, Sep. 17, 1976, abandoned, which is a continuation of Ser. No. 497,686, Aug. 15, 1974, Pat. No. 4,016,124.

[30] Foreign Application Priority Data

Aug. 21, 1973 [GB] United Kingdom ............... 39383/73

[51] Int. Cl.$^2$ ................................................ C08K 3/40
[52] U.S. Cl. ............................................. 260/29.6 M

[58] Field of Search .................... 260/29.6 H, 29.6 M; 526/317

[56] References Cited

U.S. PATENT DOCUMENTS

| | | | |
|---|---|---|---|
| 2,945,013 | 7/1960 | Ott .................................. | 260/29.6 H |
| 3,635,915 | 1/1972 | Gale ............................... | 260/29.6 H |
| 3,655,605 | 4/1972 | Smith ............................. | 260/29.6 M |
| 3,741,926 | 6/1973 | Jurecie .......................... | 260/29.6 M |

FOREIGN PATENT DOCUMENTS 1316129  5/1973  United Kingdom .

Primary Examiner—Paul R. Michl
Attorney, Agent, or Firm—Jacobs & Jacobs

[57]  ABSTRACT

A cement-forming liquid suitable for use as a component of a poly(carboxylate) cement comprises an aqueous solution of a copolymer of acrylic acid, the copolymer having an average molecular weight of less than 20,000, and the solution having a viscosity of less than 50 poise.

20 Claims, No Drawings

CEMENTS

This is a continuation of Ser. No. 724,394, filed Sept. 17, 1976 now abandoned, which was a continuation of Ser. No. 497,686, filed Aug. 15, 1974, now U.S. Pat. No. 4,016,124, issued Apr. 5, 1977.

This invention relates to poly(carboxylate) cements and is particularly concerned with cements for use in dentistry.

The materials known as dental cements have many applications in dentistry including use as filling materials for restoring teeth and for cementing inlays and crowns into place in the tooth, providing a base and/or lining in a tooth cavity, providing a temporary fixing for the bonds of orthodontic appliances to the teeth and sealing root canals after endodontic treatment. In recent years the traditional phosphate dental cements, i.e. zinc phosphate dental cement and dental silicate cement, have been to some extent displaced for many applications by the new "poly(carboxylate) dental cements", in which the cement-forming liquid is an aqueous solution of a poly(carboxylic acid). Such cements are described and claimed in our British Pat. Nos. 1,139,430 and 1,316,129, and in British Pat. No. 1,304,987.

The poly(carboxylate) cements have improved acid and stain resistance over conventional dental cements and have the additional advantage that they do not irritate pulpal tissues. However, it has been found in practice that the viscosity of the cement-forming liquid occasionally causes the poly(carboxylate) cement to be more difficult to mix than conventional materials and an improvement in this respect would be desirable. In addition, aqueous solutions of poly(carboxylic acids) sometimes gel on standing for long periods and have to be discarded.

According to the present invention an improvement in the mixing and storage properties of poly(carboxylate) cement is obtained by using as the cement-forming liquid an aqueous solution of a low molecular weight copolymer of acrylic acid.

The present invention provides a cement-forming liquid suitable for use as a component of a poly(carboxylate) cement comprising an aqueous solution of a copolymer of acrylic acid, the copolymer having an average molecular weight of less than 20,000 and the solution having a viscosity as hereinafter defined of less than 50 poise.

The invention further provides a process for the production of a cement-forming liquid suitable for use as a component of a poly(carboxylate) cement which comprises copolymerising acrylic acid with an unsaturated aliphatic compound in aqueous solution at a temperature above 85° C.

The invention also provides a poly(carboxylate) cement pack comprising as one component a water soluble copolymer of acrylic acid, the copolymer having an average molecular weight of less than 20,000 and as another component a cement powder which will react with the acrylic acid copolymer in the presence of water to give a plastic mass which hardens to form a poly(carboxylate) cement.

In addition, the invention also provides a process for the preparation of a poly(carboxylate) cement which comprises mixing a water soluble copolymer of acrylic acid, the copolymer having an average molecular weight of less than 20,000, with a cement powder which will react with the acrylic acid copolymer in the presence of water to give a mass than remains plastic long enough to be formed into a desired shape prior to hardening as a poly(carboxylate) cement.

In this specification viscosity is defined as the viscosity measured with a falling sphere viscometer of a freshly prepared aqueous solution of the acrylic acid co-polymer at 21° C.

Cement packs in accordance with this invention preferably comprise the acrylic acid copolymer in the form of an aqueous solution which may contain from 20% to 65% by weight of the acrylic acid copolymer.

The poly(carboxylate) cement pack may be a two-part pack in which the weight ratio of powder to liquid in the two parts is preferably from 0.5:1 to 5:1 so that when the entire contents of the packs are mixed together a rapidly hardening cement is obtained. In another embodiment the pack may contain the powder and the liquid in separate capsules, the total amount of powder in the pack and the total amount of liquid in the pack being in the appropriate ratio. In a further embodiment, both components may be encapsulated in the same capsule in the desired ratio, provided that steps are taken to prevent premature reaction.

In the above mentioned embodiments the cement powder is from 15% to 85% by weight, the acrylic acid copolymer is from 3% to 50% and the water is from 5% to 70% by weight of the total composition.

It is found that when the components are mixed together a plastic mass can be obtained which sets rapidly in the mouth (1.5 to 10 mins. following completion of preparation).

The acrylic acid copolymer preferably has an average molecular weight of from 5,000 to 19,000 and most preferably around 10,000. In this specification the average molecular weight is defined as being that determined by calculation based on viscometric measurements. First, the intrinsic viscosity is calculated from the measured viscosity of a 1% m/v solution of the copolymer in aqueous molar sodium chloride by the Solomon-Ciuta equation:

$$[\eta] = \frac{\sqrt{2}}{c} \sqrt{\eta \text{ specific} - {}^{ln}\eta \text{ relative}} ,$$

where c is concentration in grams/100 ml. solution. The average molecular weight M is then calculated from the empirical equation:

$$[\eta] = 1.91 \times 10^{-4} M^{0.65}$$

This equation has been established by the absolute methods of light scattering and ultracentrifuge sedimentation.

The acrylic acid copolymer is preferably present in the cement-forming liquid in an amount sufficient to produce an aqueous solution containing at least 30% by weight of the copolymer, and preferably from 40% to 65% by weight of copolymer. The preferred solutions have a viscosity as hereinbefore defined of from 5 to 40 poise, and particularly from 10 to 30 poise.

The preferred copolymers are those prepared by the copolymerisation of acrylic acid with other unsaturated aliphatic carboxylic acid, for example 2-chloro acrylic acid, 3-chloro acrylic acid, 2-bromo acrylic acid, 3-bromo acrylic acid, methacrylic acid, itaconic acid, maleic acid, glutaconic acid, aconitic acid, citraconic acid, mesaconic acid, fumaric acid, and tiglic acid.

Other suitable monomers for copolymerising with acrylic acid include unsaturated aliphatic compounds such as for example acrylamide, acrylonitrile, vinyl chloride, allyl chloride, vinyl acetate, and 2-hydroxy ethyl methacrylate. Ter- and higher polymers may be used if desired. Particularly preferred are the copolymers of acrylic acid and itaconic acid. Preferably the mole ratio of acrylic acid to unsaturated aliphatic compound is from 19:1 to 2:1.

If desired there may be added to the liquid a water soluble chelating agent as described in Wilson et al U.S. Ser. No. 595,039.

The cement-forming liquid is mixed with a cement powder to form a plastic mass which sets rapidly in the mouth. The cement powder is an ion-leachable powder which can react with a poly(carboxylic acid) in the presence of water and which may for example comprise a simple metal oxide, preferably one that has been deactivated by heat treatment, for example zinc oxide, to which there may be added up to about 10% by weight of other metal oxides such as, for example, magnesium oxide. Alternatively, the cement powder may comprise a fused oxide made by heating a mixture of simple oxides to fusion temperature, or an oxide glass, for example one comprising calcium or sodium oxide with alumina, silica and phosphorus pentoxide. For dental applications however, the cement powder most preferably comprises a fluoroaluminosilicate glass powder as described and claimed in our British Pat. No. 1,316,129 wherein the ratio by weight of silica to alumina is from 1.5:2.0 and the ratio by weight of fluorine to alumina is from 0.6:2.5, or wherein the ratio by weight of silica to alumina is from 0.5:1.5 and the ratio by weight of fluorine to alumina is from 0.25:2.0. The fluoroalumino-silicate glasses may be prepared by fusing mixtures of silica ($SiO_2$) alumina ($Al_2O_3$), cryolite ($Na_3AlF_6$) and fluorite ($CaF_2$) in the appropriate proportions at a temperature above 950° C. Suitable methods for preparing the glasses are described in the aforementioned British Patent. For other applications, good results may also be obtained using a silicate mineral as described in Crisp et al U.S. Ser. No. 529,390.

Fluorides, bacteriostatic agents or antibiotics may be added to the cement powder in minor amounts as desired to provide some antibacterial or anticariogenic action in dental use.

The degree of fineness of the cement powder should preferably be such that it produces a smooth cement paste which sets within an acceptable period when mixed with the cement-forming liquid. Preferably the degree of fineness of the powder is such that it will pass through a 150 mesh B.S. sieve, and most preferably such that it passes through a 350 mesh B.S. sieve.

In dental applications, the cements of this invention are designed to be made by the practitioner immediately prior to use as in the conventional manner. Thus, the materials in the one or two part pack are brought together and mixed forming a plastic mass which can be cast, moulded or otherwise formed into the required shape during the brief period in which the mixture retains its plastic properties. For example, a quantity of the cement-forming liquid sufficient to make up one small batch of cement may easily be withdrawn from its container using a dental spatula or similar instrument or extruded from a tube or like container and this may be mixed with a quantity of a dental cement powder on a suitable surface. The components can be mixed quite rapidly to give a uniform mass which commences to harden in a few minutes and is usually set within 10 minutes of mixing. In addition to the other parameters mentioned above, the rate of hardening and strength of the final product are determined by the powder/liquid ratio which is preferably as high as possible compatible with adequate working time. The optimum ratio for a particular powder and liquid may be determined readily with preliminary experiments. Too little or too much powder normally results in a mixture that is more difficult to form into a desired shape. Particularly good results have been obtained with powder/liquid ratios in the range 1:1 to 4:1. Careful matching of the powder and the liquid components will enable a plastic mass to be obtained of the desired consistency which will harden in an acceptable time.

The acrylic acid copolymer solution may be prepared by polymerising the appropriate monomers in aqueous solution in the presence of a free radical initiator, for example, ammonium persulphate and various chain transfer agents, for example, isopropyl alcohol to give a solution containing up to about 30% by weight of the copolymer. Such a solution may then be concentrated, if necessary. The copolymer solutions of this invention are preferably prepared by polymerising the monomers in boiling water, that is to say at temperatures at or around 100° C., and particularly at temperatures of from 90° to 100° C. These temperatures are considerably higher than those customarily used in conventional aqueous polymerisation techniques.

In addition to traditional dental use, the poly(carboxylate) cements of the present invention may also find application in preventive dentistry for example, their adhesive properties may permit their use as pit and fissure sealants, and as fillers for cervical lesions.

The uses of the poly(carboxylate) cements are not limited to dentistry and they may find application for example in other forms of surgery, particularly orthopaedic surgery where they may be used to assist in the resetting of fractured bone material, and in grouting compositions.

The invention is illustrated by the following Examples. In the Examples, film thickness is measured by the method of British Standard 3364, and consistency, setting time, compressive strength and solubility by the method of British Standard 3365 (1969). Diametral strength is measured by the method of Williams & Smith J. Dent Res. 50, 1971, 436–442. Working time is measured using a 28 gram Gilmore needle of 1.05 mm. diameter, taking the time at which the needle no longer makes an impression of 0.5 mm.

EXAMPLE 1

This Example describes the preparation of a poly(carboxylate) cement using as the cement-forming liquid an aqueous solution of a 1:4 mole ratio copolymer of itaconic acid and acrylic acid. 2.5 parts by weight of ammonium persulphate and 200 parts by volume of water are placed in a three-necked round bottomed flask fitted with a condenser, and nitrogen is bubbled through the solution.

Solution A is 72.3 parts by weight of acrylic acid, 20 parts by volume of propan-2-ol and 100 parts by volume of water. Solution B is 2.5 parts by weight of ammonium persulphate and 60 parts by volume of water. 32.7 parts by weight of itaconic acid is divided into 24 equal parts. The solution in the flask is heated to boiling and additions of solutions A and B and itaconic acid are made at approximately 5 minute intervals. After the completion of the additions the solution is heated for a further two hours. The reaction product is concentrated to 50% w/w concentration by vacuum distillation at 40°–45°.

There is produced an aqueous solution of an acrylic acid/itaconic acid copolymer having a molecular weight of 18,000 and a viscosity of 26 poise.

A fluoroaluminosilicate glass powder is prepared as described in British patent application No. 1,316,129, by mixing together 175 parts by weight of silica, 100 parts by weight of alumina, 30 parts by wiehgt of cryolite, 207 parts by weight of calcium fluoride, 32 parts by weight of aluminium fluoride, and 60 parts by weight of aluminium phosphate, and heating to a temperature of 1,150° C. The glass is ground to a mesh size of 350 BSS. mesh.

The powder and the liquid, containing 5% by weight of tartaric acid based on the weight of the copolymer, are mixed together in the ratio of 3.75 grams of powder to 1 milliliter of liquid. The properties of the resulting cement are given in Table 1.

TABLE 1

| Consistency (mm) | 25 |
|---|---|
| Working time (min) | 2.75 |
| Setting time (min) | 3.25 |
| Compressive strength (Nmm$^{-2}$) | 194 |

Stability of liquid (before onset of gelling) > 16 months.

EXAMPLE 2

This Example describes the preparation of a poly(carboxylate) cement using as the cement-forming liquid an aqueous solution of a 1:2 mole ratio copolymer of itaconic acid and acrylic acid.

The procedure of Example 1 is repeated using 55.7 parts by weight of acrylic acid and 49.8 parts by weight of itaconic acid. There is obtained a 50% w/w aqueous solution of an acrylic acid/itaconic acid copolymer containing 47.4% itaconic acid units, having a molecular weight of 10,000 and a viscosity of 11 poise.

Two dental cements are prepared using the same glass powder as in Example 1 in different powder/liquid ratios. These correspond to a filling grade and a luting grade. The properties of the cements are given in Table 2.

TABLE 2

| | filling grade | luting grade |
|---|---|---|
| Powder/liquid ratio (g.ml.$^{-1}$) | 4.0 | 2.75 |
| Consistency (mm) | 27 | 26 |
| Working time (min) | 2.75 | 5 |
| Setting time (min) | 3.75 | 5.25 |
| Compressive strength (Nmm$^{-2}$) | 154 | 128 |
| Diametral strength (Nmm$^{-2}$) | 10 | 8.8 |
| Film thickness (microns) | | 83 |

Stability of liquid (before onset of gelling) > 19 months.

EXAMPLE 3

The cement-forming liquid of Example 2 is used to prepare further poly(carboxylate) cements according to the present invention using the same cement powder but varying the powder/liquid ratio. The results are given in Table 3:

TABLE 3

| Powder/liquid ratio (g.ml.$^{-1}$) | 2.5 | 3.0 | 3.5 |
|---|---|---|---|
| Consistency (mm.) | 25 | 33.5 | 31 |
| Working time (min) | 5 | 3.25 | 3 |
| Setting time (min) | 4.75 | 4.25 | 4 |

TABLE 3-continued

| Compressive strength (Nmm$^{-2}$) | 133 | 162 | 175 |
|---|---|---|---|
| Diametral strength (Nmm$^{-2}$) | 11.4 | 12.2 | 12.9 |
| Film thickness (microns) | 43 | — | — |
| Solubility (%) | — | 0.54 | 0.36 |

EXAMPLE 4

This Example describes a comparison between the cement-forming liquid of the present invention and certain prior art materials.

1. The procedure described in Example 1 of British Pat. No. 1,304,987 is repeated. There is obtained an aqueous solution containing 26% by weight of a copolymer of acrylic acid and itaconic acid. The copolymer contains 36% of itaconic acid units and has an average molecular weight of 41,000. The solution is evaporated to 50% concentration as described in the prior specification.

2. A 50% solution of polyacrylic acid is prepared as described in British Pat. No. 1,139,430. The polyacrylic acid has an average molecular weight of 23,000.

3 and 4. Samples of solutions according to Examples 1 and 2 of the present application are prepared and evaporated to 50% concentration.

The solutions are mixed with samples of fluoroaluminosilicate glass powder prepared according to British Pat. No. 1,316,129 in a powder to liquid ratio sufficient to give a consistency of about 25 mm. The results for the four liquids are tabulated below:

TABLE 4

| | (1) | (2) | (3) | (4) |
|---|---|---|---|---|
| Viscosity | 46 | 50 | 26 | 11 |
| Stability of liquid at 21° C. (months) | >12 | 3 to 6 | >18 | >19 |
| Powder to liquid ratio (g.ml.$^{-1}$) | 3 | 3 | 3.75 | 4 |
| Consistency (mm.) | 25 | 25 | 25 | 27 |
| Working time (min) | 2 | 2 | 2.75 | 2.75 |
| Setting time (min) | 5.25 | 5.25 | 3.25 | 3.75 |
| Compressive strength (Nmm$^{-2}$) | — | 165 | 194 | 154 |
| Diametral strength (Nmm$^{-2}$) | — | 13.9 | | 10 |

It can be seen from Table 4 that cement-forming liquids according to the present invention have a substantially greater stability than polyacrylic acid, and are considerably less viscous than prior art materials. In addition, they provide a further important improvement in that the working time is increased and the setting time is decreased. This is particularly useful in dental applications where a dentist requires adequate time to form the cement into the appropriate shape, but thereafter desires the cement to harden as soon as possible.

We claim:

1. A poly(carboxylate) cement pack comprising as one component a water-soluble copolymer of acrylic acid and an unsaturated aliphatic carboxylic acid selected from the group consisting of methacrylic acid, aconitic acid, maleic acid, tiglic acid, fumaric acid and mesaconic acid, the mole ratio of acrylic acid to unsaturated aliphatic carboxylic acid in said copolymer being from 19:1 to 2:1, the copolymer having an average molecular weight of from 5,000 to 19,000 and as another component a fluoroaluminosilicate glass cement powder which will react with the acrylic acid copolymer in the presence of water to give a plastic mass which hardens to form a poly(carboxylate) cement.

2. A cement pack according to claim 1, in which the acrylic acid copolymer is in the form of an aqueous solution containing from 20% to 65% by weight of the acrylic acid copolymer.

3. A cement pack according to claim 1, that comprises from 15% to 85% by weight of the cement powder, from 3% to 50% by weight of the acrylic acid copolymer and from 5% to 70% by weight of water.

4. A cement pack according to claim 2, in which the weight ratio of cement powder to liquid is from 0.5:1 to 5:1.

5. A cement pack according to claim 2, in which the solution has a viscosity as hereinbefore defined of from 5 to 40 poise.

6. A cement pack according to claim 1, that comprises a water soluble chelating agent.

7. A cement pack according to claim 1, in which the degree of fineness of the cement powder is such that it will pass through a 150 mesh B.S. sieve.

8. A process for the preparation of a poly(carboxylate) cement which comprises mixing a water-soluble copolymer of acrylic acid and an unsaturated aliphatic carboxylic acid selected from the group consisting of methacrylic acid, aconitic acid, maleic acid, tiglic acid, fumaric acid and mesaconic acid, the mole ratio of acrylic acid to unsaturated aliphatic carboxylic acid in said copolymer being from 19:1 to 2:1, the copolymer having an average molecular weight of from 5,000 to 19,000 with a fluoroaluminosilicate glass cement powder which will react with the acrylic acid copolymer in the presence of water to give a mass that remains plastic long enough to be formed into a desired shape prior to hardening as a poly(carboxylate) cement.

9. A process according to claim 8, in which the acrylic acid copolymer is in the form of an aqueous solution containing from 20% to 65% by weight of the acrylic acid copolymer.

10. A process according to claim 9, in which the solution has a viscosity as hereinbefore defined of from 5 to 40 poise.

11. A process according to claim 8, that is carried out in the presence of a water soluble chelating agent.

12. A process according to claim 8, in which the cement powder has a degree of fineness such that it will pass through a 150 mesh B.S. sieve.

13. A process according to claim 9, in which the powder and liquid components are mixed in a powder to liquid ratio of from 1:1 to 4:1.

14. A poly(carboxylate) cement consisting essentially of the reaction product of the reaction between a copolymer of acrylic acid and an unsaturated aliphatic carboxylic acid selected from the group consisting of methacrylic acid, aconitic acid, maleic acid, tiglic acid, fumaric acid and mesaconic acid, the mole ratio of acrylic acid to unsaturated aliphatic carboxylic acid in said copolymer being from 19:1 to 2:1, said copolymer having an average molecular weight of from 5,000 to 19,000 and a fluoroaluminosilicate glass cement powder in the presence of water.

15. The poly(carboxylate) cement according to claim 14, in which the copolymer is in the form of an aqueous solution containing from 20% to 65% by weight of the acrylic acid copolymer.

16. The poly(carboxylate) cement according to claim 14, in which the weight ratio of cement powder to liquid is from 0.5:1 to 5:1.

17. The poly(carboxylate) cement according to claim 14, in which the copolymer has a viscosity as hereinbefore defined of from 5 to 40 poise.

18. The poly(carboxylate) cement according to claim 14, in which said reaction is carried out in the presence of a chelating agent.

19. The poly(carboxylate) cement according to claim 14, in which the cement powder has a degree of fineness such that it will pass through a 150 mesh B.S. sieve.

20. The poly(carboxylate) cement according to claim 14, in which the powder and liquid components are mixed in a powder to liquid ratio of from 1:1 to 4:1.

* * * * *